(12) United States Patent
Cohen et al.

(10) Patent No.: US 9,110,053 B2
(45) Date of Patent: Aug. 18, 2015

(54) DRIED BLOOD SPOTTING PAPER DEVICE AND METHOD

(75) Inventors: Susan L. Cohen, Dana Point, CA (US); Wilford C. Downs, Dana Point, CA (US); William C. Hudson, Tustin, CA (US); Paul Boguszewski, London (GB)

(73) Assignee: Agilent Technologies, Inc., Santa Clara, CA (US)

( * ) Notice: Subject to any disclaimer, the term of this patent is extended or adjusted under 35 U.S.C. 154(b) by 618 days.

(21) Appl. No.: 12/860,669

(22) Filed: Aug. 20, 2010

(65) Prior Publication Data

US 2012/0045792 A1   Feb. 23, 2012

(51) Int. Cl.
  *G01N 1/30* (2006.01)
  *G01N 33/52* (2006.01)
  *B01L 3/00* (2006.01)
  G01N 33/558 (2006.01)
  G01N 1/28 (2006.01)

(52) U.S. Cl.
  CPC ............ *G01N 33/523* (2013.01); *B01L 3/5023* (2013.01); *B01L 2300/021* (2013.01); *B01L 2300/126* (2013.01); *G01N 33/558* (2013.01); *G01N 2001/288* (2013.01)

(58) Field of Classification Search
  None
  See application file for complete search history.

(56) References Cited

U.S. PATENT DOCUMENTS

| | | | |
|---|---|---|---|
| 3,791,933 A * | 2/1974 | Moyer et al. | 435/287.8 |
| 4,042,335 A * | 8/1977 | Clement | 422/423 |
| 4,227,249 A | 10/1980 | Hansen | |
| 4,299,812 A | 11/1981 | Coombes | |
| 4,774,192 A | 9/1988 | Terminiello et al. | |
| 4,790,797 A | 12/1988 | Allert | |
| 4,816,224 A * | 3/1989 | Vogel et al. | 422/422 |
| 4,842,855 A * | 6/1989 | Youngner et al. | 424/520 |
| 4,891,319 A * | 1/1990 | Roser | 435/188 |
| 4,968,604 A * | 11/1990 | Beatty | 435/7.92 |
| 5,204,267 A * | 4/1993 | Sangha et al. | 436/14 |
| 5,415,758 A | 5/1995 | Comeau | |
| 5,427,953 A | 6/1995 | Yee | |
| 5,432,097 A | 7/1995 | Yourno | |
| 5,460,057 A | 10/1995 | Ostrup | |
| 5,496,626 A | 3/1996 | Hamajima et al. | |
| 5,508,200 A | 4/1996 | Tiffany et al. | |
| 5,516,487 A | 5/1996 | Rosenthal et al. | |
| 5,609,749 A * | 3/1997 | Yamauchi et al. | 205/777.5 |
| 5,652,148 A * | 7/1997 | Doshi et al. | 436/178 |
| 5,714,389 A * | 2/1998 | Charlton et al. | 436/514 |
| 5,871,942 A * | 2/1999 | Larka et al. | 435/7.32 |
| 6,054,282 A * | 4/2000 | Garman | 435/7.2 |
| 7,585,641 B2 * | 9/2009 | Bandla et al. | 435/7.8 |
| 7,837,939 B2 * | 11/2010 | Tung et al. | 422/410 |
| 2005/0209532 A1 | 9/2005 | Wandell et al. | |
| 2005/0220677 A1 * | 10/2005 | Sangha | 422/102 |
| 2012/0103421 A1 * | 5/2012 | Grenz et al. | 137/1 |
| 2012/0107951 A1 * | 5/2012 | Grenz et al. | 436/178 |
| 2012/0130195 A1 * | 5/2012 | Martin et al. | 600/300 |
| 2014/0373644 A1 * | 12/2014 | Iraneta et al. | 73/863.23 |

OTHER PUBLICATIONS

D'Avolio et al., "HPLC-MS method for the quantification of nine anti-HIV drugs from dry plasma spot on glass filter and their long term stability in different conditions", Journal of Pharmaceutical and Biomedical Analysis 52 (2010) 774-780.*
Li, W. et al.; Dried blood spot sampling in combination with LC-MS/MS for quantitative analysis of small molecules; Biomedical Chromotography 2010; 24: 49-65, John Wiley & Sons, Ltd. 17 pages.
D'Avolio, A. et al.; HPLC-MS method for the quantification of nine anti-HIV drugs from dry plasma spot on glass filter and their long term stability in different conditions, Journal of Pharmaceutical and Biomedical Analysis 52 (2010) 774-780, Elsevier B.V. doi: 10.1016/j.jpba.2010.02.026.
Campbell, D. et al.; Rapid genotyping of mutant mice using dried blood spots for polymerase chain reaction (PCR) analysis; Brain Research Protocols 1 (1997) 117-123; Elsevier Science B.V., PH S1385-299X(96)00019-0.
EPO; EPO form 2001 (EP Office Action) mailed Dec. 4, 2013 for corresponding EP Application No. 11173363.0-1408.
EPO; EPO form 1503 (EP Search Report) mailed Aug. 31, 2011 for corresponding EP Application No. 11173363.0-1408.

* cited by examiner

*Primary Examiner* — Ann Lam

(57) ABSTRACT

A dried blood-spotting device includes a carrier card having a window therethrough along with a punchable glass fiber paper disposed in the window for a uniform absorption of a blood droplet sample into a homogeneous circular sport. The glass fiber paper is configured for enabling improved analysis for small molecules by liquid chromatography/mass spectrometry of punched specimens of the sample absorbed glass fiber paper.

5 Claims, 3 Drawing Sheets

DRIED BLOOD SPOTTING PAPER DEVICE AND METHOD

BACKGROUND OF THE INVENTION

Dry bloodspot sampling has been successful for facilitating remote site sampling collection and transport of samples to a laboratory for analysis.

The methods and materials in this art have been the subject of many patents, including U.S. Pat. No. 5,516,487, which describes the use of various antibiotics or preservatives in combination with a cotton fiber filter paper, as well as the use of multiple application zones on the filter paper, which are isolated from each other by perforations in the filter paper; U.S. Pat. No. 5,508,200, which describes the use of filter papers in a complex integrated analytical system and measurement of chemical reactions on the filter paper matrix; U.S. Pat. No. 5,432,097, concerning digestion of the filter paper with cellulose so that recovery of intact cells can be achieved; U.S. Pat. No. 5,427,953, which concerns measurement of a heavy metal (e.g., lead) from blood samples collected on filter paper; U.S. Pat. No. 5,204,267, which describes preservation of blood samples collected on various filter matrices for glucose analysis; U.S. Pat. No. 4,816,224, which is directed to a multiple layer device for separating plasma or serum from a blood sample collected for glucose analysis; U.S. Pat. No. 4,299,812, pertaining to an improved thyroid function test; and U.S. Pat. No. 4,227,249, which primarily concerns a drying procedure and its effect on the results of an assay measuring somatomedin.

Other patents describing the use of certain blotting materials used in biological assay methods include U.S. Pat. Nos. 5,496,626; 5,460,057; 5,415,758; 4,790,797; and 4,774,192.

However, none of the cited patents relate to, or teach, the use of blood spotting papers useful in association with the analysis of blood for small molecules, such as pharmaceutical compounds and drugs.

The present invention includes the discovery of unexpectedly improved and superior analysis results utilizing the materials that are commercially available and presumed to provide only equivalent results. Thus, the present invention significantly improves the accuracy of the detection of small molecules in blood.

SUMMARY OF THE INVENTION

A dry blood-spotting device in accordance with the present invention generally includes a carrier card having a window therethrough along with a punchable glass fiber paper disposed in the window for uniform absorption of a blood droplet sample into a homogeneous circular spot.

Importantly, the glass fiber is configured for enabling analysis of small molecules for which specimens of the sample absorbed glass fiber paper.

More particularly, the glass fiber paper is untreated and configured without cellulose to enable analysis of small molecules such as pharmaceutical compounds and drugs. Examples of such drugs include METOPROLOL or (RS)-1-(Isopropylamino)-3-[4-(2-methoxyethyl)phenoxy]propan-2-ol, PROPRANOLOL or (RS)-1-(1-methylethylamino)-3-(1-naphthyloxyl)propan-2-ol, AMITRIPTYLINE or 3-(10,11-dihydro-5H-dibenzo[a,d]cycloheptene-5-ylidene)-N,N-dimethylpropan-1-amine, and CLOZAPINE or 8-chloro-11-(4-methylpiperazin-1-yl)-5H-dibenzo[b,e][1,4]diazepine.

Indicia may be disposed on the glass fiber paper for indicating placement of the blood samples on the glass fiber paper for the convenience of the analyst.

To insure uniform absorption of blood through the paper, a fiber paper thickness of about 0.03 mm may be utilized.

A method in accordance with the present invention for assaying pharmaceutical compounds in a liquid blood sample generally includes providing a material for absorbing the liquid blood sample, applying the liquid blood sample to the material, and allowing the liquid blood sample to dry into a dried sample.

Thereafter, the dried sample is punched from the material and assayed for pharmaceutical compounds. As hereinabove described in connection with a device in accordance with the present invention, the material includes a cellulose free glass fiber paper, which is supported in the window of a carrier.

BRIEF DESCRIPTION OF THE DRAWINGS

The advantages and features of the present invention will be better understood by the following description when considered in conjunction with the accompanying drawings in which.

DETAILED DESCRIPTION

Figure 1:
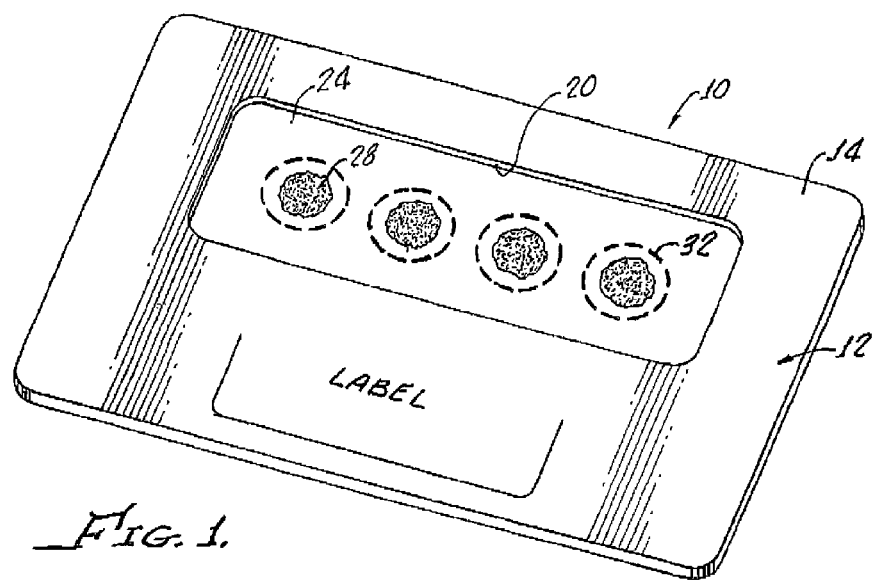
FIG. 1 is a perspective view of a dried blood-spotting (DBS) device in accordance with the present invention generally showing a carrier along with a glass fiber paper disposed in a window along with an absorbed blood droplet sample in homogeneous circular spot.
Figure 2:
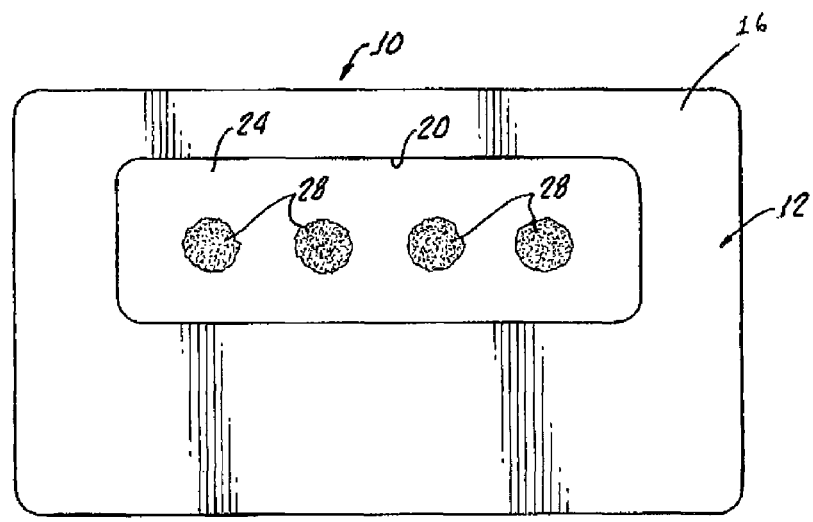
FIG. 2 is a plan view of an opposite side of the device shown in FIG. 1 illustrating the uniform penetration of the blood sample through the fiber paper.
Figure 3:
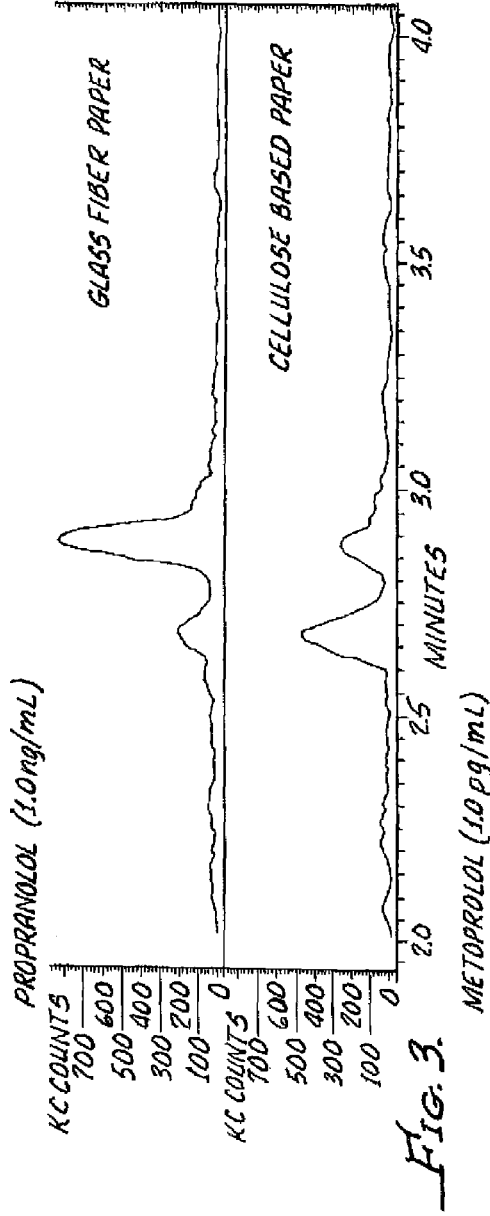
FIG. 3 is a plot of a liquid chromatography/mass spectrometry (LC/MS) analysis (of PROPRANOLOL) utilizing the glass fiber paper in accordance with the present invention as compared to results for a cellulose-based paper.
Figure 4:
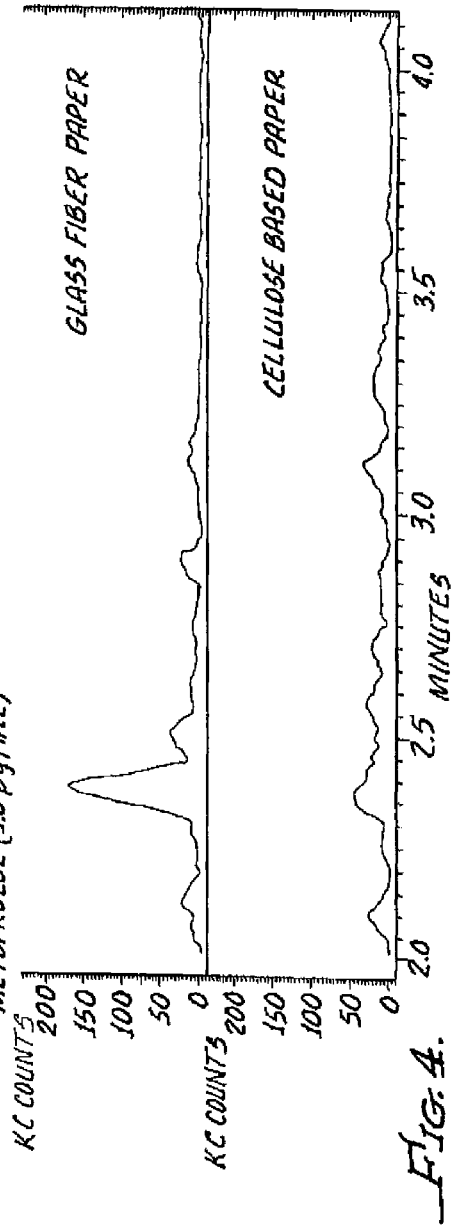
FIG. 4 are plots of LC/MS analyses similar to that shown in FIG. 3 for METOPROLOL.
Figure 5:
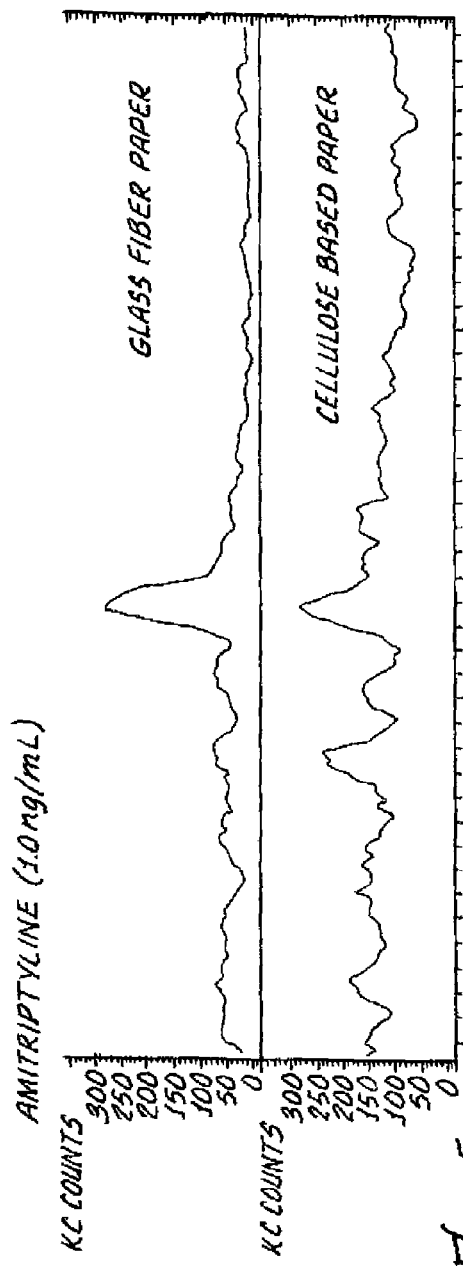
FIG. 5 are plots of LC/MS analyses similar to that shown in FIG. 3 for AMITRIPTYLINE.
Figure 6:
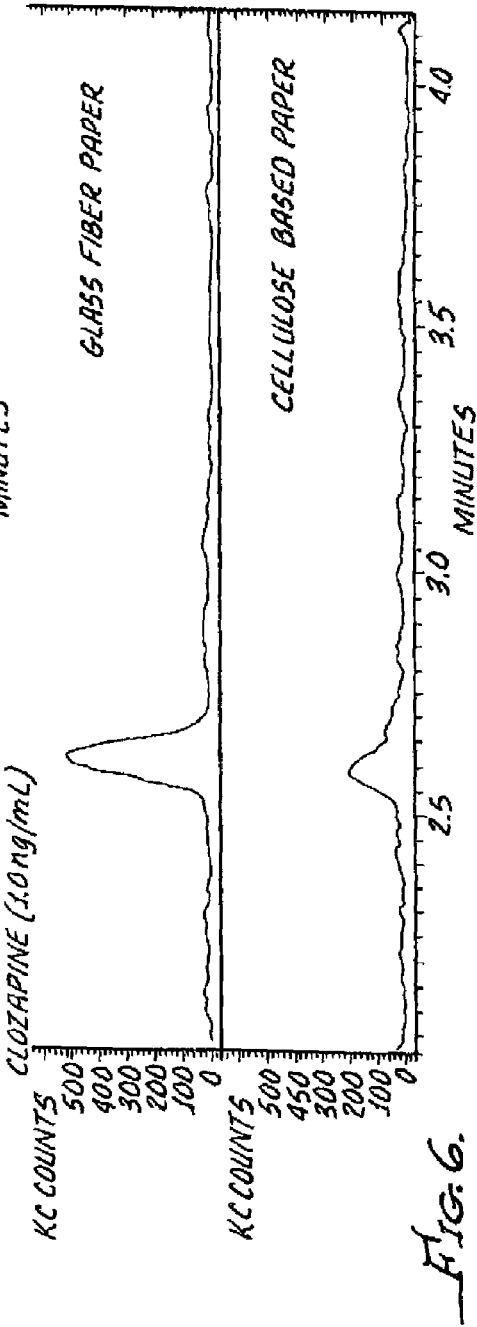
FIG. 6 are plots of LC/MS analyses similar to FIG. 3 for CLOZAPINE.

With reference to FIGS. 1 and 2, there is shown a dry blood-spotting device 10 in accordance with the present invention, which generally includes a carrier card 12 having a front face 14 and a back face 16 along with a window 20 therethrough.

A punchable glass fiber paper is disposed in the window. Uniform absorption of a blood droplet sample 28, which is absorbed into a homogeneous circular spot with the fiber paper 24 having a thickness, such as, for example, about 0.03 mm, for enabling complete absorption of the blood droplet sample 28 through the glass fiber paper 24 as illustrated in FIG. 2. Indicia 32 may be provided on the glass fiber paper 24 for assisting in placement of multiple blood droplet samples 28.

The glass fiber paper is configured for enabling analysis of small molecules from punched specimens (not separately shown) of the sample 28 absorbed and the glass fiber paper 24.

A great number of spotting materials have been utilized for blood specimen collection. These include but are not limited to cellulose materials, glass fibers, glass fiber/cellulose composites, nylon, polyesters, polypropylene, nitrocellulose, modified polyether polyethersulfone, polyvinyl chloride, as well as modified natural or synthetic fibers, laminated materials, etc.

From this huge selection of materials it has been discovered that the use of untreated glass fiber, which is cellulose free, as a blotting material for absorbing blood facilitates and improves the capability of measurement for small molecules such as pharmaceutical compounds and drugs by liquid chromatography/mass spectrometry (LC/MS).

The card 12 may have a nominal size of approximately 2 inches (5.08 cm) by 3 inches (7.62 cm) and may be formed from a chipboard material. The window 20 enables the user to apply blood spots 28 directly onto the glass fiber paper 24 without removing it from the carrier 12. The blood spot 28 is then dried and punched from the glass fiber paper 24 and extracted in a laboratory for analysis of small molecules such as pharmaceutical compounds and drugs of abuse, etc.

The use of fiber paper prevents wicking away of blood from the point of application and therefore enables a uniform circle absorption allowing maximal sample amount in a small spot.

As hereinabove noted, the glass fiber paper 24 is made from untreated glass fiber and it has been determined that nitrocellulose can cause secondary interactions and lead to poor drug recovery in the analysis. The glass fiber paper 24 does not suffer from these interactions and therefore provides better recoveries over nitrocellulose counterparts.

The effectiveness of the device 10 and method in accordance with the present invention can be seen from the following example, which includes analysis for pharmaceutical compositions for the treatment of blood pressure/hypertension such as METOPROLOL and PROPRANOLOL, compositions for the treatment of depression such as AMITRIPETYLINE, and compositions for the treatment of schizophrenia such as CLOZAPINE utilizing an untreated cellulose free glass fiber paper, such as is available from Hollingsworth and Vose of East Walpole, Mass., part no. DG17005.

Further benefits of the use of a glass fiber paper are manifested in that other papers tend to create a halo effect around the main spot, whereas glass fiber paper provides for a homogeneous spot, both vertically and/or horizontally as shown in FIGS. 1 and 2. In addition, cellulose based paper requires a significantly more force to punch a disc from the paper than glass fiber paper.

Glass fiber paper 24 is fairly soft in texture compared to cellulose but is, however, rigid enough not to tear in the cardboard carrier card 12. This softness provides for a more easily punched material versus cellulose.

EXAMPLE a. 20 µl of Human Blood was spied to 0.5 ng/mL and 1.0 ng/mL of, METOPROLOL, CLOZAPINE, and AMITRIPTYLINE.
b. A 3 mm disk was punched and placed into a centrifuge tube.
c. 100 µl of 0.1% formic acid in methanol was added and vortexed. Sample was evaporated to dryness and reconstituted with 100 µl of 0.1%.

LC/MS Conditions
Column—Pursuit XRS$^{1.9}$ Diphenyl 30 mm×2.0 mm
Mobile Phase—

| d. | A: 5 mM Ammonium formate | B: MeOH |
|---|---|---|

Pump Program—Flow rate 200 µl/min.

| $t_{0 - 0:15}$ | A: 90%, B: 10% |
| $t_{3.0 - 3.5}$ | A: 10%, B" 90% |
| $t_{3.5 - 4:00}$ | A: 90%, B: 10% |

Run Time=4:00 minutes.
Drying gas: 350° C., 25 psi
Vortex Gas: 300° C., 10 psi
Nebulizing Gas: 55 psi
Pol: Pos
Compounds

| Compound | Q1 ion | Product ion | CE |
|---|---|---|---|
| METOPROLOL | 268.0 | 116.0 | −17.5 eV |
| PROPRANOLOL | 260.1 | 116.0 | −17.0 eV |
| AMITRIPTYLINE | 278.1 | 233.0 | −16.5 eV |
| CLOZAPINE | 327.0 | 270.0 | −22.0 eV |

The results shown in FIGS. 3-6 clearly demonstrate improved recovery of pharmaceutical compounds in human blood. Better signal to noise ratios were achieved for PROPRANOLOL, METOPROLOL, AMITRIPTYLINE, and CLOZAPINE using glass fiber paper.

Although there has been hereinabove described a specific dried blood spotting paper device and method in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element, which is not specifically disclosed herein. Accordingly, any and all modifications, variations or equivalent arrangements, which may occur to those skilled in the art, should be considered to be within the scope of the present invention as defined in the appended claims.

What is claimed is:

1. A dried blood spotting device comprising:
a carrier card comprising a front face having a window therethrough, and a back face; and
punchable, untreated cellulose-free glass fiber paper disposed between the front face and the back face such that the glass fiber paper is exposed in the window, wherein the front face and the back face are effective for supporting the glass fiber paper during punching thereof, and the glass fiber paper is configured for uniform absorption of a blood droplet sample into a homogeneous circular spot without a halo thereabout, and for enabling improved analysis for small molecules by liquid chromatography/mass spectrometry of punched specimens of the sample absorbed glass fiber paper.

2. The device according to claim 1, wherein said small molecules comprise pharmaceutical compounds and drugs.

3. The device according to claim 2, wherein the pharmaceutical compounds are selected from a group consisting of (RS)-1-(Isopropylamino)-3-[4-(2-methoxyethyl)phenoxy]propan-2-ol, (RS)-1-(1-methylethylamino)-3-(1-naphthyloxy)propan-2-ol, 3-(10,11-dihydro-5H-dibenzo[a,d]cyclohepten-5-ylidene)-N,N-dimethylpropan-1-amine, and 8-chloro-11-(4-methylpiperazin-1-yl)-5H-dibenzo[b,e][1,4]diazepine.

4. The device according to claim 1, wherein the glass fiber paper is of a thickness enabling complete absorption of the blood droplet sample through the glass fiber paper.

5. The device according to claim 4, wherein the glass fiber paper has a thickness of about 0.03 mm.

* * * * *

UNITED STATES PATENT AND TRADEMARK OFFICE
CERTIFICATE OF CORRECTION

| | |
|---|---|
| PATENT NO. | : 9,110,053 B2 |
| APPLICATION NO. | : 12/860669 |
| DATED | : August 18, 2015 |
| INVENTOR(S) | : Susan L. Cohen et al. |

It is certified that error appears in the above-identified patent and that said Letters Patent is hereby corrected as shown below:

IN THE SPECIFICATION

In column 1, line 61, delete "naphthyloxyl)" and insert -- naphthyloxy) --, therefor.

IN THE CLAIMS

In column 4, line 54-55, in claim 3, delete "naphthyloxyl)" and insert -- naphthyloxy) --, therefor.

Signed and Sealed this
Fifteenth Day of March, 2016

Michelle K. Lee
*Director of the United States Patent and Trademark Office*